United States Patent
Zhang et al.

(10) Patent No.: US 10,504,040 B2
(45) Date of Patent: Dec. 10, 2019

(54) ANNEALED SPARSITY VIA ADAPTIVE AND DYNAMIC SHRINKING

(71) Applicant: NEC Laboratories America, Inc., Princeton, NJ (US)

(72) Inventors: Kai Zhang, Monmouth Junction, NJ (US); Zhengzhang Chen, Princeton Junction, NJ (US); Haifeng Chen, Monmouth Junction, NJ (US); Guofei Jiang, Princeton, NJ (US)

(73) Assignee: NEC Corporation (JP)

( * ) Notice: Subject to any disclaimer, the term of this patent is extended or adjusted under 35 U.S.C. 154(b) by 874 days.

(21) Appl. No.: 15/160,280

(22) Filed: May 20, 2016

(65) Prior Publication Data

US 2016/0358104 A1    Dec. 8, 2016

Related U.S. Application Data

(60) Provisional application No. 62/169,692, filed on Jun. 2, 2015.

(51) Int. Cl.
   *G06N 20/00*        (2019.01)
(52) U.S. Cl.
   CPC ................... *G06N 20/00* (2019.01)
(58) Field of Classification Search
   CPC ........ G06N 20/00; G06N 99/00; G06F 19/34; G06F 17/18; G06F 17/50; G06F 15/18; G06F 9/48
   See application file for complete search history.

(56) References Cited

U.S. PATENT DOCUMENTS 8,924,315 B2 *  12/2014  Archambeau .......... G06N 7/005
                                                   706/12

OTHER PUBLICATIONS

Ali Jalali et al., A Dirty Model for Multiple Sparse Regression, IEEE Transactions on Information Theory, vol. 59, No. 12, Dec. 2013 (Year: 2013).*

John Duchi et al., Boosting with Structural Sparsity, Proceedings of the 26 th International Conference on Machine Learning, Montreal, Canada, 2009 (Year: 2009).*

(Continued)

*Primary Examiner* — Hal Schnee
*Assistant Examiner* — Randall K. Baldwin
(74) *Attorney, Agent, or Firm* — Joseph Kolodka

(57) ABSTRACT

Systems and methods are provided for acquiring data from an input signal using multitask regression. The method includes: receiving the input signal, the input signal including data that includes a plurality of features; determining at least two computational tasks to analyze within the input signal; regularizing all of the at least two tasks using shared adaptive weights; performing a multitask regression on the input signal to create a solution path for all of the at least two tasks, wherein the multitask regression includes updating a model coefficient and a regularization weight together under an equality norm constraint until convergence is reached, and updating the model coefficient and regularization weight together under an updated equality norm constraint that has a greater $l_1$-penalty than the previous equality norm constraint until convergence is reached; selecting a sparse model from the solution path; constructing an image using the sparse model; and displaying the image.

20 Claims, 7 Drawing Sheets

(56) References Cited

OTHER PUBLICATIONS

Jianpeng Xu et al., ORION: Online Regularized multi-task regressiON and its application to ensemble forecasting, IEEE International Conference on Data Mining (Year: 2014).*

Zhang, K. et al., "Annealed Sparsity via Adaptive and Dynamic Shrinking" ACM (Jul. 2016) pp. 1-10.

* cited by examiner

ANNEALED SPARSITY VIA ADAPTIVE AND DYNAMIC SHRINKING

RELATED APPLICATION INFORMATION

This application claims priority to provisional U.S. Application. No. 62/169,692 filed on Jun. 2, 2015, incorporated herein by reference in its entirety.

BACKGROUND

Technical Field

The present invention relates to multitask learning and, more particularly, to sparse multitask regression in multitask learning.

Description of the Related Art

Sparse learning has received a large great deal of interest in high-dimensional data analysis due to its model interpretability and low-computational cost.

One method used in conjunction with sparse learning is the Least Absolute Shrinkage and Selection Operator (LASSO) method. The LASSO method is method of regression analysis in which both regularization and variable selection are performed. This enhances prediction accuracy and interpretability in statistical models.

Among the various techniques, adaptive $l_1$-regularization is an effective framework to improve the convergence behavior of the LASSO, by using varying strengths of regularization across different features. Additionally, the adaptive structure makes it very powerful in modelling grouped sparsity patterns as well, being particularly useful in high-dimensional multitask problems. However, choosing an appropriate, global regularization weight is still an open problem.

In sparse multitask learning, an adaptive LASSO method has been used to solve the problem of joint feature selection in multiple tasks. However, how to determine regularization weights used in the adaptive LASSO algorithm is still an open problem for multitask learning. Currently, the weights are computed based on another, independent estimator, which can lead to a sub-optimal result.

Mixed-norm regularization has been used to solve the sparse multitask learning problem, by enforcing group-wise L1 norm regularization to achieve group-wise feature selection. However, it can only enforce group-wise sparsity, not within-group sparsity.

SUMMARY

According to an aspect of the present principles, a method is provided for acquiring data from an input signal using multitask regression. The method includes receiving, into a memory, the input signal, the input signal including data that includes a plurality of features. The method further includes determining at least two computational tasks to analyze within the input signal and regularizing all of the at least two tasks using shared adaptive weights. The method yet further includes performing, using a processor, a multitask regression on the input signal to create a solution path for all of the at least two tasks, wherein the multitask regression includes updating a model coefficient and a regularization weight together under an equality norm constraint until convergence is reached to produce a sparse model in the solution path, and updating the model coefficient and regularization weight together under an updated equality norm constraint that has a greater $l_1$-penalty than the previous equality norm constraint until convergence is reached to produce another sparse model in the solution path. The method additionally includes selecting a sparse model from the solution path, constructing an image using the sparse model, and displaying the image on a display.

According to another aspect of the present principles, a system is provided for acquiring data from an input signal using multitask regression. The system includes a memory to receive the input signal, the input signal including data that includes a plurality of features. The system further includes a processor, the processor being configured to: determine at least two computational tasks to analyze within the input signal; regularize all of the at least two tasks using shared adaptive weights; perform a multitask regression on the input signal to create a solution path for all of the at least two tasks, select a sparse model from the solution path; and construct an image using the sparse model. The processor is further configured to perform the multitask regression by: updating a model coefficient and a regularization weight together under an equality norm constraint until convergence is reached to produce a sparse model in the solution path; and updating the model coefficient and regularization weight together under an updated equality norm constraint that has a greater $l_1$-penalty than the previous equality norm constraint until convergence is reached to produce another sparse model in the solution path. The system additionally includes a display for displaying the constructed image.

According to yet another aspect of the present principles, a non-transitory computer-readable storage medium including a computer-readable program for assigning labels to an object is provided, wherein the computer-readable program when executed on a computer causes the computer to perform the steps of: receiving, into a memory, the input signal, the input signal including data that includes a plurality of features; determining at least two computational tasks to analyze within the input signal; regularizing all of the at least two tasks using shared adaptive weights; performing, using a processor, a multitask regression on the input signal to create a solution path for all of the at least two tasks, selecting a sparse model from the solution path; constructing an image using the sparse model; and displaying the image on a display. The multitask regression includes: updating a model coefficient and a regularization weight together under an equality norm constraint until convergence is reached to produce a sparse model in the solution path; and updating the model coefficient and regularization weight together under an updated equality norm constraint that has a greater $l_1$-penalty than the previous equality norm constraint until convergence is reached to produce another sparse model in the solution path.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
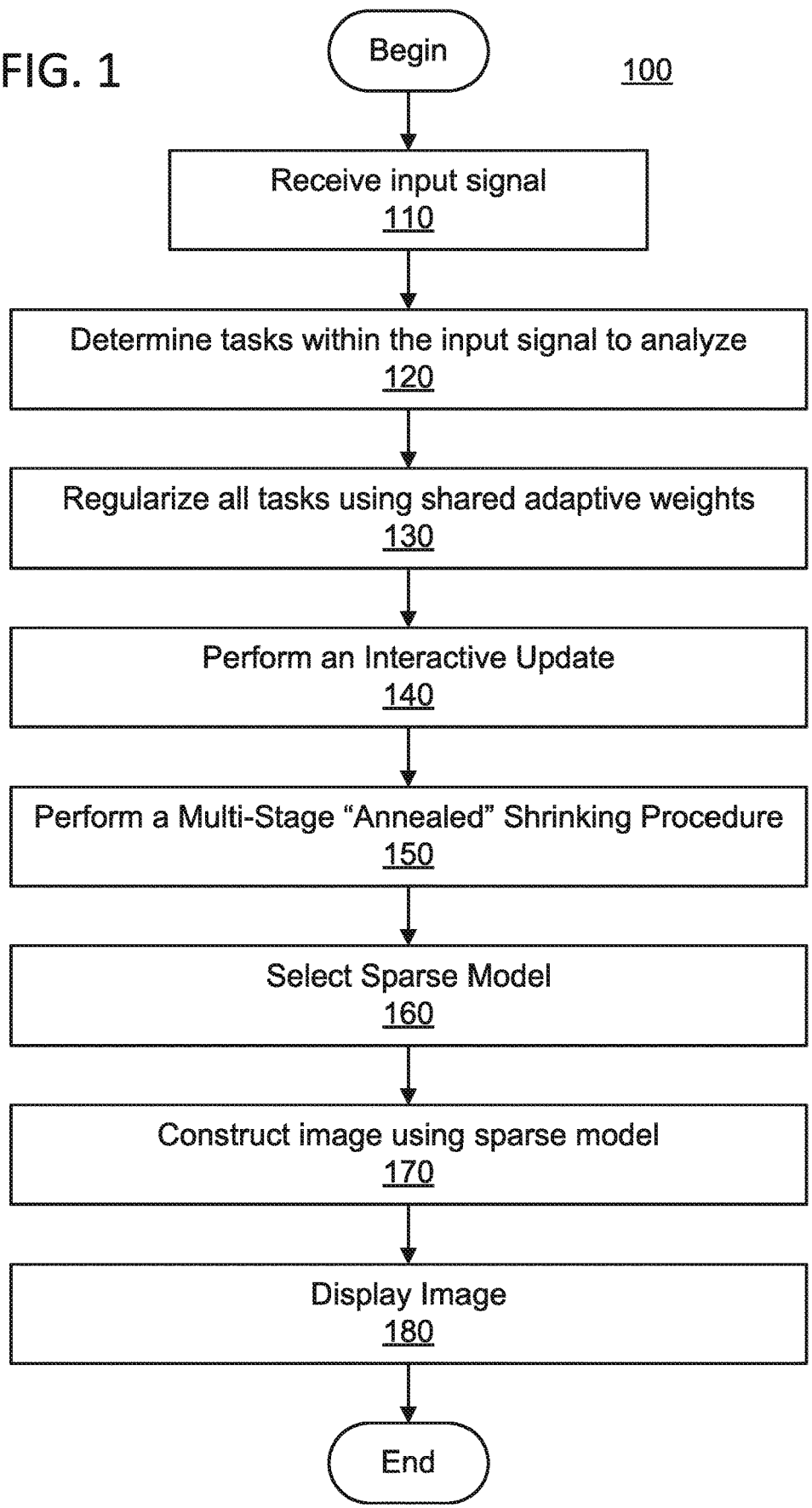
FIG. 1 is a flowchart illustrating a high-level method for iteratively computing regularization weights together with model coefficients in a data driven manner, together with an annealing procedure, in accordance with an embodiment of the present principles.

In accordance with the present principles, systems and methods are provided for achieving "annealed sparsity" by designing a dynamic shrinking scheme that concurrently optimizes regularization weights and model coefficients in sparse (multitask) learning.

With the rapid development of data acquisition technologies in various science and engineering domains, such as, e.g., imaging, physics, biology, and computer networks, access to an unprecedented amount and quality of digital data has become a reality. In this modern paradigm, a significant challenge for data discovery is the immense number of features available for representing objects. For example, a high-resolution image is composed of millions of pixels; the micro-array data in a human genomic study typically includes tens of thousands of gene expressions; in movie recommendation systems, the number of movies can be in the tens of millions. How to identify truly relevant features in the immense feature pools for accurate learning and prediction has become one of the key challenges in data mining.

Sparse regression has recently emerged as a powerful tool for high-dimensional data analysis, especially in removing irrelevant variables and identifying a parsimonious subset of covariates for predicting a target.

For example, given a response vector $y=[y_1, y_2, \ldots, y_n]^T$ and predictors $X \in \mathbb{R}^{n \times D}$, where, without loss of generality, the data is centered, sparse regression and, in particular, the Least Absolute Shrinkage and Selection Operator (LASSO) method, solves the following regularized linear regression problem:

$$\min_\beta \|X\beta - y\|_2^2 + \lambda |\beta|_1, \quad (1)$$

where $\beta \in \mathbb{R}^{D \times 1}$ is the regression coefficient vector.

The $l_1$-norm $|\beta|_1$ is used to enforce the sparsity of the solution, resulting in the model being easier to interpret. Meanwhile, recent advances in solving the non-smooth, convex LASSO problem have made it computationally extremely efficient. Therefore, the LASSO, and related methods, have been applied with great success in a number of domains, including, e.g., bioinformatics, imaging and computer vision, and signal processing.

It has been shown that LASSO can perform automatic variable selection because the $l_1$-penalty is singular at the origin. It has also been shown that variable selection with the LASSO is consistent only under certain conditions. Namely, there are scenarios in which the LASSO selection is not consistent. One proposed solution to this problem is to use adaptive weights to regularize the model coefficients along different features, as $$\min_\beta \|X\beta - y\|_2^2 + \lambda \cdot |\hat{w} \odot \beta|_1 \quad (2)$$

where $\hat{w} \in \mathbb{R}^{D \times 1}$ is the regularization weight, and $|\hat{w} \odot \beta|_1 = \Sigma_i \hat{w}_i |\beta_i|$. In an embodiment, each feature is one dimension of the input signal, namely, one column of the input data matrix X. Namely, each dimension of $\beta$ is penalized differently instead of sharing a single regularization parameter $\lambda$, as in LASSO. The regularization weights $\hat{w}$ can be chosen as $\hat{w} = |\beta_{ols}|^{-\gamma}$, where $\beta_{ols}$ is the ordinal least-square solution, and $\gamma$ is a positive number. Such choice renders the oracle property of the adaptive LASSO estimator in concurrent variable selection and prediction.

Besides improving the asymptotic behavior of sparse model estimation, the adaptive LASSO can also be quite useful in imposing structured sparsity patterns, in particular in high-dimensional multi-task learning by sharing the same adaptive weight across different tasks. Therefore, it has gained a relatively large amount of research interest from various domains. However, choosing an optimal regularization weight vector $\hat{w}$ (2) can be much more challenging than selecting a single regularization parameter $\lambda$ (1). The former has a significantly larger search space, and is the key to the superior performance of adaptive LASSO.

In an embodiment of the present principles, a method is provided by which the model coefficients and adaptive regularization weights are concurrently computed in $l_1$-regularized regression, rather than computing them separately, as has been done in the past.

In an embodiment, an alternating optimization framework is adopted to establish closed-form relations between model coefficients and regularization weights (under an equality norm-constraint of the latter). In an embodiment, by adopting this framework, the two sets of parameters are optimized iteratively, until an equilibrium state is obtained upon convergence.

The interactive updating scheme can acquire greater flexibility in tuning the sparse model. In an embodiment, to further improve its convergence and reduce the sensitivity on initial conditions, an "annealed" shrinking procedure is performed, wherein, throughout the interactive updates between model coefficients and regularization weights, the global magnitude of $l_1$-penalization is gradually strengthened by adjusting the equality norm-constraint on the regularization weight vector. In an embodiment, by starting from a dense solution, the system progresses through a series of micro-stages that continuously sparsify and ameliorate it. In this "annealing" process, features behave like particles: in the "high-temperature" beginning, all features have the freedom to compete with each other and position themselves in the model; however, when the system gradually "cools down," fewer and fewer features have the ability to preserve their energy; finally, only those features that survive the dynamic competing process will be selected.

For example, consider the following linear regression problem with the design matrix $X \in \mathbb{R}^{n \times D}$, where n is the sample size and D is the dimensionality, and the target response vector $y \in \mathbb{R}^{n \times 1}$y. In this example, adaptive weight vector $w=[w_1, w_2, \ldots, w_D]^T$ is used to regularize over different covariates, as $$\min_{w,B} \|X\beta - y\|_2^2 + |w^{-\gamma} \odot \beta| \quad (3)$$

$$\text{s.t. } \Sigma_d w_d = w, w_d \geq 0, \quad (4)$$

wherein $\beta \in \mathbb{R}^{D \times 1}$ is the model, $w \in \mathbb{R}^{D \times 1}$ is the regularization weight vector, and $|w^{-\gamma} \odot \beta| = \Sigma_{d=1}^{D} w_d^{-\gamma} \cdot |\beta_d|$. In an embodiment of the present principles, both parameters are optimized.

The equality norm-constraint $\Sigma_d w_d = \omega$ is quite useful in controlling the global strength of regularization (in an average sense). To see this, note that the regularization imposed on the dth feature is $w_d^{-\gamma}$ (3). If $\gamma$ is positive, the larger the $\omega$ and the smaller the average strength of the $l_1$-penalty. If $\gamma$ is negative, the larger the $\omega$ and the larger the average strength of $l_1$-penalty. Due to this equality norm-constraint (4), the flexibility of "annealing" the whole system to improve the state of solution is acquired.

Embodiments described herein may be entirely hardware, entirely software or including both hardware and software elements. In a preferred embodiment, the present invention is implemented in software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

Each computer program may be tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Referring now in detail to the figures in which like numerals represent the same or similar elements and initially to FIG. 1, a high-level method 100 for iteratively computing regularization weights together with model coefficients in a data driven manner, together with an annealing procedure, is illustratively depicted in accordance with one embodiment of the present principles.

Similar to the annealing processes of materials science, method 100 describes a method by which "annealed sparsity" is achieved by designing a dynamic shrinking scheme that concurrently optimizes regularization weights and model coefficients in sparse (multitask) learning.

At block 110, multitask data is input. In an embodiment, the multitask data can is in the form of an electronic signal. The data can include, e.g., imaging data, text, etc. In an embodiment, there are a multitude of computational tasks within the multitask data.

At block 120, a number of tasks are chosen for analyzation, wherein each task is composed of a design matrix.

At block 130, shared adaptive weights are used to regularize over all of the tasks. In an embodiment, each task is a regression problem of the form defined in equations (3) and (4); different tasks can have different data properties but will also share something in common such as, e.g., their model coefficients will share similar sparsity structures.

At block 140, regularization weights are updated interactively with model coefficients for a particular equality norm constraint. In an embodiment, the regularization weights and the model coefficients are updated until convergence is reached, producing a sparse model in the solution path. The interactive updating scheme can acquire greater flexibility in tuning the sparse model. In an embodiment, this process enables a global regularization structure to be improved upon. An example of this process is described, in further detail, in FIG. 2.

At block 150, a dynamic annealed shrinking process is applied in which interactions are coupled with gradually boosted $l_1$-regularization by adjusting an equality norm-constraint. In an embodiment, once the interactive update of block 140 achieves convergence, the interactive update is repeated with an equality norm constraint that has a greater $l_1$-penalty than the equality norm constraint used in the previous interactive update. This achieves an "annealing" effect to further improve model selection and further renders interesting shrinking behavior in the whole solution path. An example of this process is described, in further detail, in FIG. 3.

At block 160, a sparse model from the solution path is selected. In an embodiment, a cross-validation can be used to select the best model along the solution path. Other methods, in accordance with the present principles, may also be used to select the best model.

At block 170, an image is constructed from the sparse model selected at block 160, and, at block 180, the image is displayed onto, e.g., a display, a graphical user interface, etc.

In an embodiment, method 100 is used in conjunction with functional Magnetic Resonance Imaging (fMRI) data, in which task level constraints (namely explicit task/subject labels) are available. In an embodiment, the fMRI data is input at block 110. Method 100 can be used to impose task level constraints such that, in order to extract meaningful network structures from individual subjects for subsequent diagnosis, shared sparsity, as well as labels of individuals (tasks), is considered. Furthermore, method 100 can be used to perform inductive rule transfer, wherein, given a new subject without a label (healthy/diseased), estimations can be made as to whether the subject's brain network will be discriminative.

The human brain can be deemed as a large-scale network, with nodes being distinct brain regions and edges representing functional connectivity. It has been shown that, for many neuropsychiatric disorders, the brains of afflicted patients may have disrupted connectivity patterns that differ from the connectivity patterns for brains of individuals not afflicted with the disorders. Therefore, the brain functional network can serve as an informative feature for prediction of the neuropsychiatric disease status on an individual basis, which is of great clinical values.

Past studies have shown that a particular brain region predominately interacts with only a small number of other brain regions. Therefore, the true brain function network is sparse.

Spare modelling techniques have been adopted in the inference of the brain functional networks. For example, the Sparse Inverse Covariance Estimation (SICE), also known as Gaussian graphical models or graphical LASSO, has been used for functional connectivity modeling. The algorithm minimizes the negative log-likelihood of the inverse covariance matrix subject to a sparsity constraint.

Another example is the high-dimensional variable selection in graphs where the relation between one node with respect to all the rest nodes is estimated using the LASSO. The procedure goes cyclically though every node to build a global neighborhood graph.

Most of the existing methods focus on estimating the brain network independently on an individual subject. In practice, however, there is usually fMRI image (or time series) data for a larger number of subjects from the same population. This amounts to a multitask learning scenario with explicit task relations: each individual subject is one task of sparse linear regression, tasks from the same (or different) groups should also have associated models that are similar (or distinct) from each other.

Figure 2:
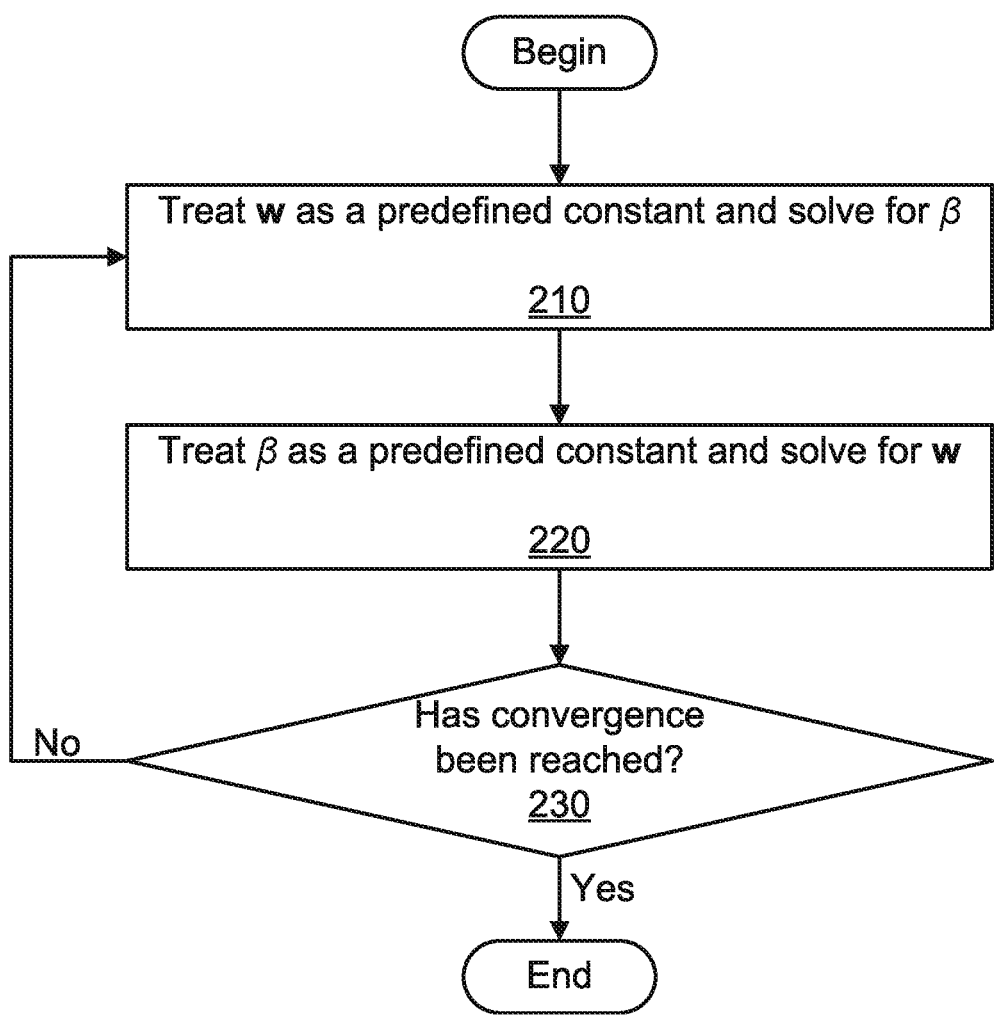
FIG. 2 is a flowchart illustrating a method for interactively updating regularization weights with model coefficients, in accordance with the present principles.

Referring now to FIG. 2, a method 140 for interactively updating regularization weights with model coefficients, in accordance with method 100 of FIG. 1, is illustratively depicted in accordance with an embodiment of the present principles.

In an embodiment, power parameter γ can be chosen either as a positive or negative real number, in comparison to the power parameter that can only be positive in the adaptive LASSO.

In a standard adaptive LASSO, the regularization weight is inversely related to some pre-computed model coefficient. However, in an embodiment according to the present principles: first, weights are carefully tuned based on previous model coefficients through norm-regularization (7); second, continuous alternating is performed instead of using a single update; and third, the strength of global regularization is annealed via the equality norm-constraint (4).

Block 210-220 describe a method by which problem (1) is solved according to an embodiment of the present principles.

For blocks 210-220, ω is treated as a predefined constant. By treating ω as a predefined constant, problem (1) is solved by alternating optimization. Namely, w is treated as a fixed constant and the equation is solved for β (block 210), then β is treated as a fixed constant and the equation is solved for w (block 220).

At block 210, w is treated as a fixed constant and the equation is solved for β, forming the following adaptive LASSO problem:

$$\min_{\beta} \|X\beta - y\|_2^2 + |w^{-\gamma} \odot \beta|, \quad (5)$$

which can be computationally converted to a standard LASSO problem.

At block 220, β is treated as a fixed constant and the equation is solved for w, forming the following constrained optimization problem (6):

$$\min_{w} \Sigma_d \beta_d \cdot w_d^{-\gamma}, \quad (6)$$

$$\theta_d = |\beta_d|.$$

Problem (6) has a closed form solution (7):

$$w_d = \left( \frac{\frac{1}{\theta_d^{1+\gamma}}}{\Sigma_{j=1}^{D} \theta_j^{\frac{1}{1+\gamma}}} \right) \omega. \quad (7)$$

Based on equation (7), the relation between the actual regularization imposed in (3), $w^{-\gamma}$, and the (absolute) value of the model coefficient, $\theta_d$ (4), can be examined.

In an embodiment, γ>0. In this embodiment, if $\theta_d$ is larger (compared with $\theta_{d'}$, d'≠d), then $w_d$ (7) is also larger, due to the positive power term 1/(1+γ), and, as a result, the regularization term $w_d^{-\gamma}$ in (3) is smaller. This leads to a weaker regularization on the d feature in the next iteration.

In an embodiment, γ<−1. In this embodiment, if $\theta_d$ is larger (compared with $\theta_{d'}$, d'≠d), then $w_d$ (7) is smaller, due to the negative power term 1/(1+γ), and, as a result, the regularization term $w_d^{-\gamma}$ in (3) is smaller since −γ>0. This leads to a weaker regularization on the d feature in the next iteration.

In an embodiment, −1<γ<0. In this embodiment, if $\theta_d$ is larger (compared with $\theta_{d'}$, d'≠d), then $w_d$ (7) is smaller, due to the positive power term 1/(1+γ), and, as a result, the regularization term $w_d^{-\gamma}$ in (3) is larger since −γ>0. This leads to a stronger regularization on the d feature in the next iteration.

As can be seen, in scenarios in which γ>0 or γ<−1, the regularization term $w_d^{-\gamma}$ and the model coefficient $\theta_d$ are inversely related to each other: a larger $\theta_d$ will lead to a smaller regularization coefficient $w_d^{-\gamma}$, and vice versa.

In scenarios in which −1<γ<0, $w_d^{-\gamma}$ and $\theta_d$ are favorably associated with each other. In other words, relevant features in the current step will be strongly penalized in the next iteration. This leads to unstable iterations. In an embodiment, this scenario is excluded from the parameter choice.

At block 230, if convergence has not been reached, blocks 210 and 220 are repeated. Once convergence has been reached, the interactive update 140 ends.

Figure 3:
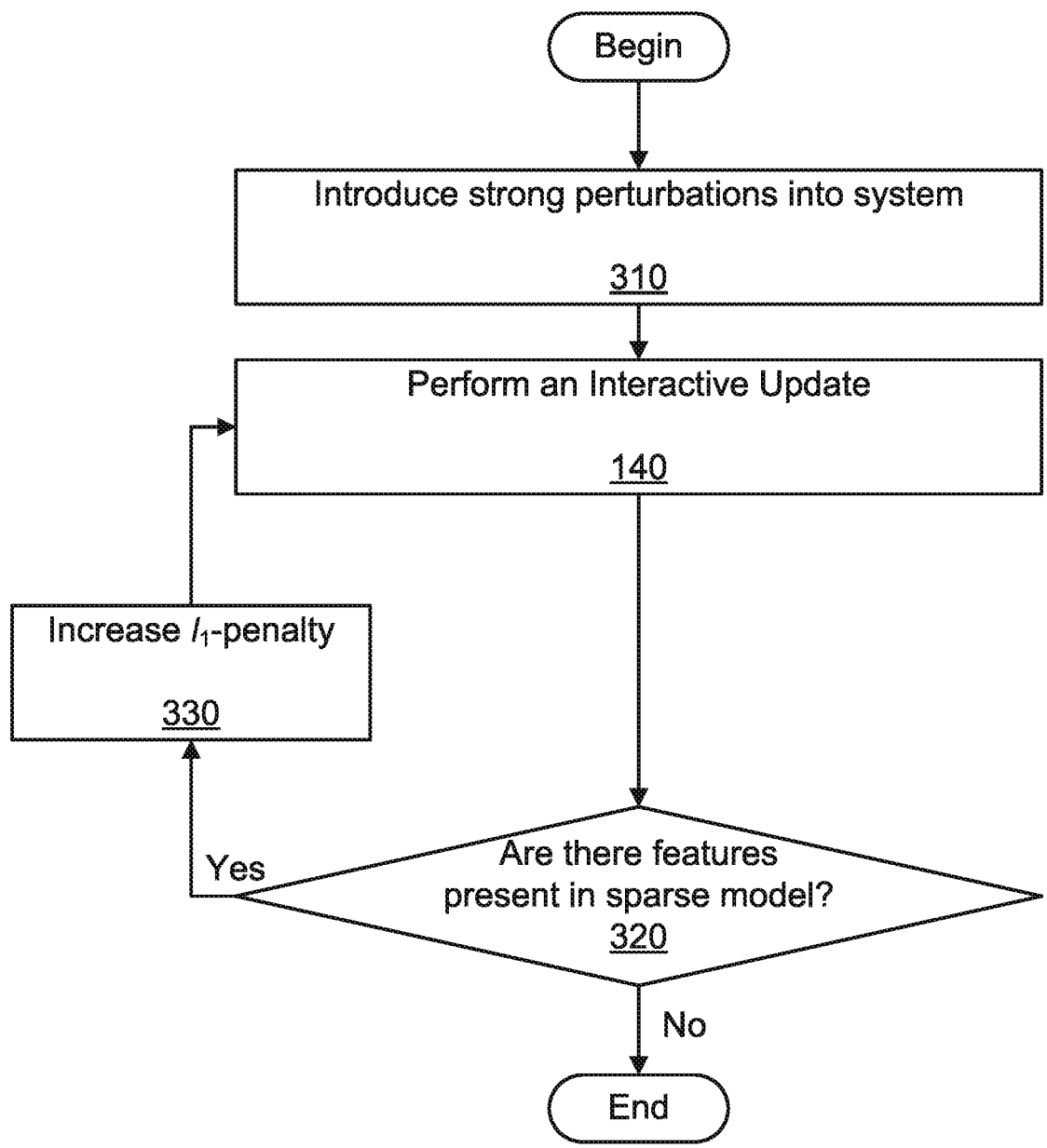
FIG. 3 is a flowchart illustrating a dynamic annealed shrinking process, in which interactions are coupled with gradually boosted $l_1$-regularization by adjusting an equality norm-constraint, in accordance with an embodiment of the present principles.

Referring now to FIG. 3, a dynamic annealed shrinking process 150, in which interactions are coupled with gradually boosted $l_1$-regularization by adjusting an equality norm-constraint, in accordance with method 100 of FIG. 1, is illustratively depicted in accordance with an embodiment of the present principles.

Interactive updates between models and adaptive weights mimic a self-adapting process that is expected to drive the whole system to a desired state. However, this optimization problem is non-convex. Therefore, in cases of bad initialization, the iterations might quickly get stuck into a local optimum.

In instances of bad initialization, dimensions with large model coefficients will keep being dominant and dimensions with small coefficients may never have a chance to regain their magnitudes.

A multi-stage shrinking process 150 is performed in order to prevent premature convergence.

At block 310, strong perturbations are introduced into the system, such that all features have the chance to be selected and compete with each other. In an embodiment, w is initialized with $|w|=\omega^\tau$, $\tau=0$.

At block 140, the interactive update 140 of FIG. 2 is performed until convergence is reached, producing a sparse model in the solution path.

At block 320, it is determined whether the sparse model produced at block 140 includes any of the multitask signal's features. If it does, the equality norm constrain is updated with an increased $l_1$-penalty, at block 330, and a subsequent interactive update (block 140) with the updated equality norm constrain (block 330) is performed with an updated norm constraint, interactively updating β (5) and w (6) until convergence. By increasing τ, the global strength of the $l_1$-penalty strengthens.

The system is gradually "cooled down" by using stronger and stronger $l_1$-penalties and iterating between β and w. Fewer and fewer features can survive in the progressive shrinking.

By repeating blocks 330 and 140, the system experiences a series of self-adjusting micro-stages sequentially before reaching the final solution. The global $l_1$-norm regularization is continuously strengthened, phase by phase, achieving an "annealing" effect. Here, each stage is indexed by τ and is composed of iterations under $|w|=\omega^\tau$, $\tau=0$. Once the interactive update produces a sparse model that does not include any features of the multitask signal, the "annealing" process ends.

The global regularization strength is the averaged magnitude of regularization enforced among each dimension of the input data, which can be effectively measured by $w^{-\gamma}$. Depending on the choice of γ, in order to guarantee that the global regularization strength $w^{-\gamma}$ will gradually increase, different strategies in tuning the ω parameter are used.

In an embodiment, when γ>0, ω will initially be a large value (corresponding to a weak regularization) and gradually decrease.

In an embodiment, when γ<−1, ω will initially be a small value and gradually increase throughout the iterations.

Process 150 has many similarities with the process of annealing in materials science. In materials science, annealing is an important metal processing technique. A metal is first heated to a high temperature, which provides the energy for its atoms to break bonds and diffuse actively within crystal lattices. After maintaining a suitable temperature, the metal is gradually cooled, so that the material progresses towards its equilibrium state, with physical and chemical properties being improved. The annealing process can reduce the Gibbs-Free-Energy of the metal.

---

Algorithm 1

---

Input: multi-task data $Z = \{X^k, y^k\}_{k=1}^K$; initial norm constraint $\omega^0$; shrinking factor δ; τ = 0; initial regularization weight $$w_0^0 = \left[\frac{\omega^0}{D}, \frac{\omega^0}{D}, \ldots, \frac{\omega^0}{D}\right];$$

Output: solution path for all the k tasks
1  begin
2  |   while model is unempty do
3  |   |   t = 0;
4  |   |   while Convergence do
5  |   |   |   $B_{t+1}^\tau$ = ModelUpdate($w_t^\tau$, Z);
6  |   |   |   $w_{t+1}^\tau$ = Weight Update($B_{t+1}^\tau$, $\omega^\tau$);
7  |   |   |   t = τ +1;
8  |   |   $\omega^{\tau+1} = \omega^\tau \cdot \delta$;
9  |   |   $w_0^{\tau+1} = w_t^\tau$;
10 |   |   τ = τ+1

---

The dynamic shrinking method in Algorithm 1 very much resembles (and is indeed inspired by) an annealing process. The strength of the $l_1$-regularization can be deemed as controlling the temperature of the system: in the beginning stages, when regularization is weak, all features have the freedom to compete and position themselves in the model. This indicates that the solution is dense and that the system has a high energy. When the regularization gradually enhances, the system begins to cool down, model coefficients begin to shrink progressively, and system energy decreases. The norm constraint $|w|=\omega$ can be deemed to be controlling the "temperature" of the system: a larger ω imposes a weak regularization, meaning high temperature and energy status; a smaller ω, on the contrary, enforces low temperature and energy status.

The initial temperature of annealing should be higher than the metal recrystallization temperature. Similarly, we should also start from a high temperature, i.e., a weak regularization, such that the initial model parameters are dense. This allows different features to fully compete with each other from the beginning; if the solution is sparse already in the beginning, then the iterations will quickly get trapped at a poor local optima. In an embodiment, the densest initial solution will be the ordinary least-square solution, which corresponds to the solution of a sparse model with vanishing $l_1$-penalties.

Figure 4:
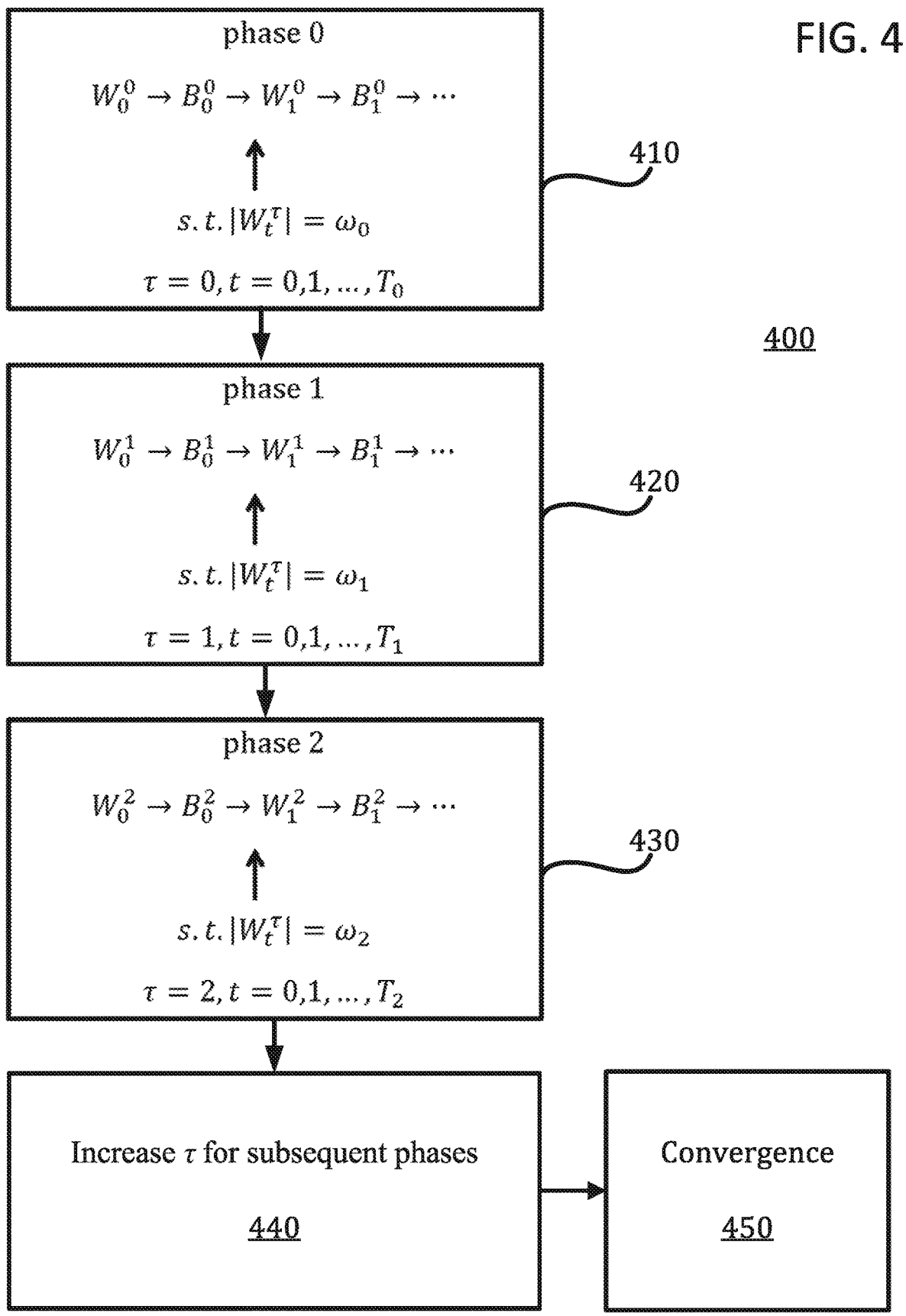
FIG. 4 is a flowchart illustrating a dynamic annealed shrinking process, in which the strength of the $l_1$-regularization gradually increases, in accordance with an embodiment of the present principles.

Referring now to FIG. 4, a dynamic annealed shrinking process 400, in which the strength of the $l_1$-regularization gradually increases, is illustratively depicted in accordance with an embodiment of the present principles.

During phase 0 (410), w is initialized with $|w|=\omega^\tau$, $\tau=0$. During time t=0, 1, $T_0$, index τ=0, such that $W_0^0 \to B_0^0 \to W_1^0 \to B_1^0$), wherein W represents the regularization weights and B represents the model coefficients. Phase 1 (420) begins after the conclusion of phase 0 (410).

During phase 1 (420), a second phase of iterations begins with updated norm constraint $|w|=\omega^\tau$, τ=1, such that, during time t=0, 1, $T_1$, $W_0^1$, $B_0^1 \to W_1^1$, $W_1^1 \to B_1^1$. By increasing τ, the global strength of the $l_1$-penalty strengthens. Phase 2 (430) begins after the conclusion of phase 1 (420).

During phase 2 (430), a third phase of iterations begins with updated norm constraint $..w|=\omega^\tau$, τ=2, such that, during time t=0, 1, $T_2$, $W_0^2 \to B_0^2 \to W_1^2 \to B_1^2$. By increasing τ, the global strength of the $l_1$-penalty once again strengthens.

In an embodiment, due to the interplay between adaptive weights w and model coefficients B, the entire solution path of B is connected, wherein each solution B is affected by its predecessor. In an embodiment, the effect of system evolution is inherited from one phase τ to the next phase τ+1, or from one iteration t to the next iteration t+1 inside a single phase.

In an embodiment, at 440, the norm constraint is updated, with increasing τ, performing further phases with the updated norm constraint. This process is repeated until convergence (450) is reached.

Figure 5:
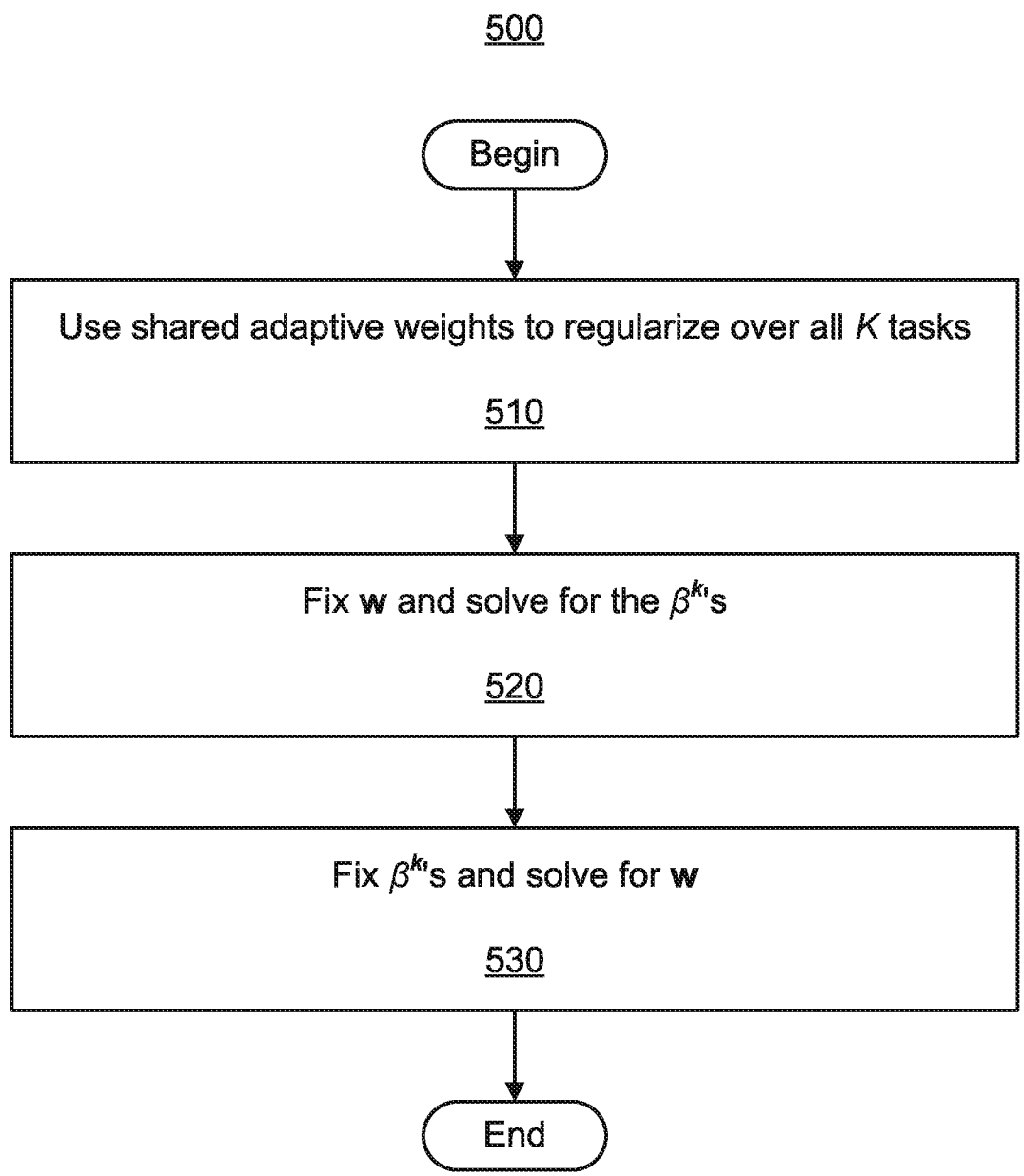
FIG. 5 is a flowchart illustrating a method for multitask regression, in accordance with an embodiment of the present principles.

Referring now to FIG. 5, a method 500 for multitask regression is illustratively depicted in accordance with an embodiment of the present principles.

In an embodiment, there are a number of k tasks, wherein each k task is composed of design matrix $X^k \in \mathbb{R}^{n^k \times D}$ target $y^k \in \mathbb{R}^{n^k \times D}$.

At block 510, shared adaptive weights $w=[w_1, w_2, \ldots, w_D]^T$ are used to regularize over all the K tasks, as $$\min_{w,B} \Sigma_{k=1}^{K} (\|X^k \beta^k - y^k\|_2^2 + |w^{-\gamma} \odot \beta^k|) \quad (8)$$

$$\text{s.t. } \Sigma_d w_d = \omega, \omega_d \geq 0, \quad (9)$$

wherein $\beta^k \in \mathbb{R}^{D \times 1}$ represents the model coefficients for the kth task for k=1, 2, . . . , K, and B=[$\beta^1, \beta^2, \ldots, \beta^K$]. Through similar derivations, we have the following procedures.

At block 520, w is fixed and the problem is solved for $\beta^k$ the $\beta^k$'s. When w is fixed, the problem becomes K independent adaptive LASSO problems, for k=1, 2, . . . , K $$\min_{\beta^k} \|X^k \beta^k - y^k\|_2^2 + |w^{-\gamma} \odot \beta^k|, \quad (10)$$

which can be easily converted to a standard LASSO.

At block 530, the $\beta^k$'s are fixed and the problem is solved for w. When the $\beta^k$'s are fixed, the problem becomes the following constrained optimization problem:

$$\min_{w} \Sigma \, \theta_d \cdot w_d^{-\gamma} \quad (11)$$

$$\theta_d = \Sigma_{k=1}^{K} |\beta_d^k|. \quad (12)$$

Problem (11) has a closed form solution, $$w_d = \left( \frac{\frac{1}{\theta_d^{1+\gamma}}}{\Sigma_{j=1}^{D} \theta_j^{\frac{1}{1+\gamma}}} \right) \quad (13)$$

In an embodiment, method 500 can conveniently handle multitask learning scenarios. This is due to the flexibility of using an adaptive regularization weight. In the following, two routines are introduced to simplify our presentation of the algorithm.

Routine 1: B=ModelUpdate(w,Z). This denotes training an adaptive LASSO with weights w (10) for each of the k tasks in $Z=\{X_k, y_k\}_{k=1}^{K}$, independently, and obtaining the model coefficients B=[$\beta^1, \beta^2, \ldots, \beta^K$].

Routine 2: w=WeightUpdate(B,ω). This denotes the process of using current models B and a specified value of ω to update the regularization weights w, as in (11) to (13).

Using these notations, the algorithm in Algorithm 1 is summarized. This is applicable to both single and multiple tasks. Here, the upper index τ denotes outer iterations, where each iteration τ corresponds to a stage with a distinct value of co. The lower index t indexes the inner iterations inside each stage. The δ is a shrinking factor that is smaller than 1 when γ>0, and a growing factor that is larger than 1 when γ<−1. The iteration will keep going until all features are removed from the model. Then, in an embodiment, a cross-validation can be used to select the best model along the solution path. Other methods, in accordance with the present principles, may also be used to select the best model.

In an embodiment, in cases of classification tasks with high-dimensional features, sparse logistic regression, $\min -\Sigma_{i=1}^{n} \ln(1+\exp[-\beta^T x_i \cdot y_i]) + |w \odot \beta|_1$, is used during the dynamic shrinking approach as well. The iterative procedures will decompose into two sub-problems: when fixing w, it becomes a standard logistic regression with adaptive $l_1$-regression; and, when fixing β, the problem is identical to (6) and can be solved accordingly.

Figure 6:
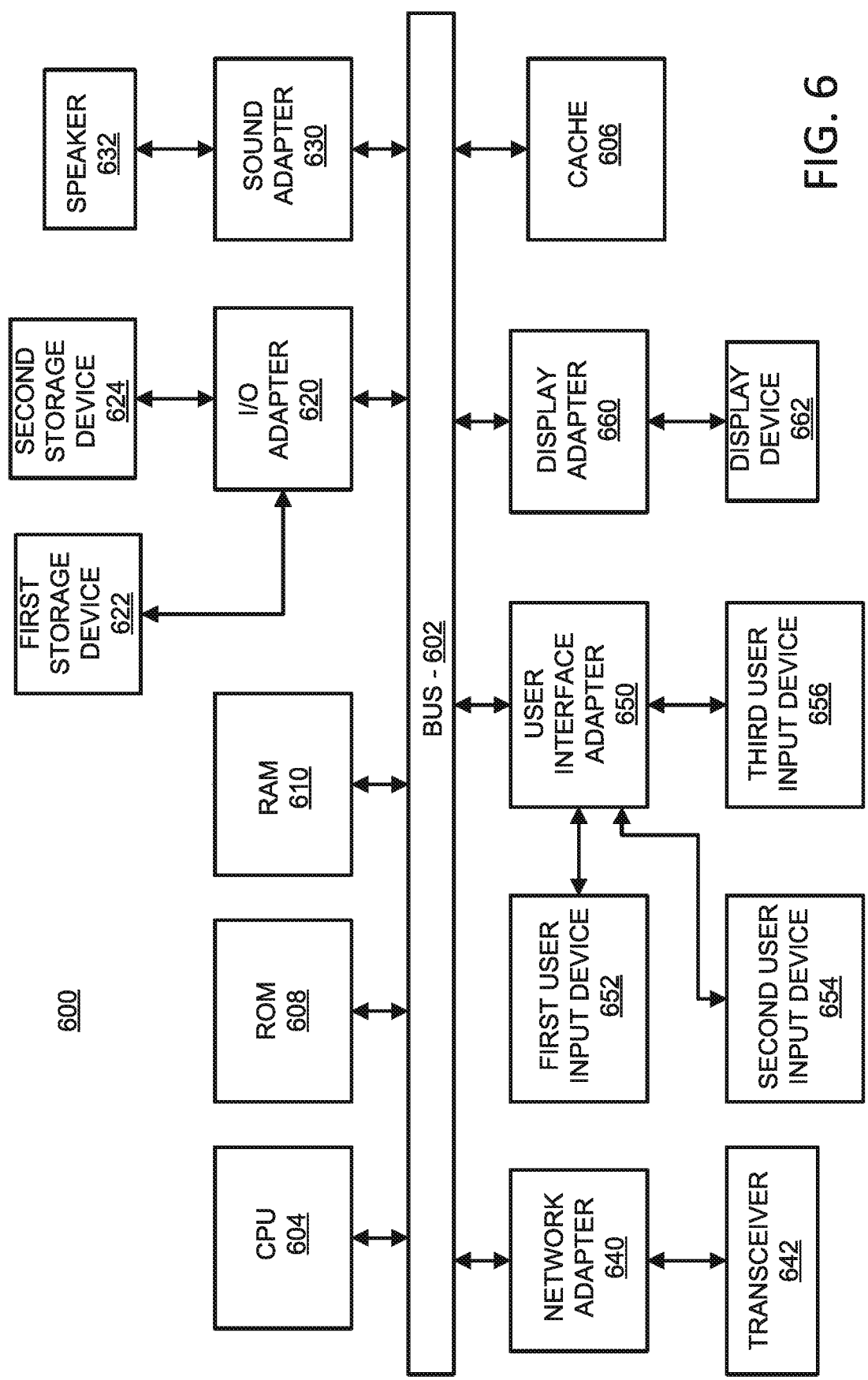
FIG. 6 is a block/flow diagram illustrating an exemplary processing system to which the present principles may be applied, in accordance with an embodiment of the present principles.

Referring now to FIG. 6, an exemplary processing system 600, to which the present principles may be applied, is illustratively depicted in accordance with an embodiment of the present principles. The processing system 600 includes at least one processor (CPU) 604 operatively coupled to other components via a system bus 602. The system bus 602 may be connected to any components via a wired or wireless connection. A cache 106, a Read Only Memory (ROM) 608, a Random Access Memory (RAM) 610, an input/output (I/O) adapter 620, a sound adapter 630, a network adapter 640, a user interface adapter 650, and a display adapter 660, are operatively coupled to the system bus 102.

A first storage device 622 and a second storage device 624 are operatively coupled to system bus 602 by the I/O adapter 620. The storage devices 622 and 624 can be any of a disk storage device (e.g., a magnetic or optical disk storage device), a solid state magnetic device, and so forth. The storage devices 622 and 624 can be the same type of storage device or different types of storage devices.

A speaker 632 is operatively coupled to system bus 602 by the sound adapter 630. A transceiver 642 is operatively coupled to system bus 602 by network adapter 640. A display device 662 is operatively coupled to system bus 602 by display adapter 660.

A first user input device 652, a second user input device 654, and a third user input device 656 are operatively coupled to system bus 602 by user interface adapter 650. The user input devices 652, 654, and 656 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 652, 654, and 656 can be the same type of user input device or different types of user input devices. The user input devices 652, 654, and 656 are used to input and output information to and from system 600. Of course, the processing system 600 may also include other elements (not shown), as readily contemplated by one of skill in the art, as well as omit certain elements. For example, various other input devices and/or output devices can be included in processing system 600, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 600 are readily contemplated by one of ordinary skill in the art given the teachings of the present principles provided herein. Moreover, it is to be appreciated that system 200, described with respect to FIG. 2 is a system for implementing respective embodiments of the present principles. Part or all of processing system 600 may be implemented in one or more of the elements of system 700 of FIG. 7.

Figure 7:
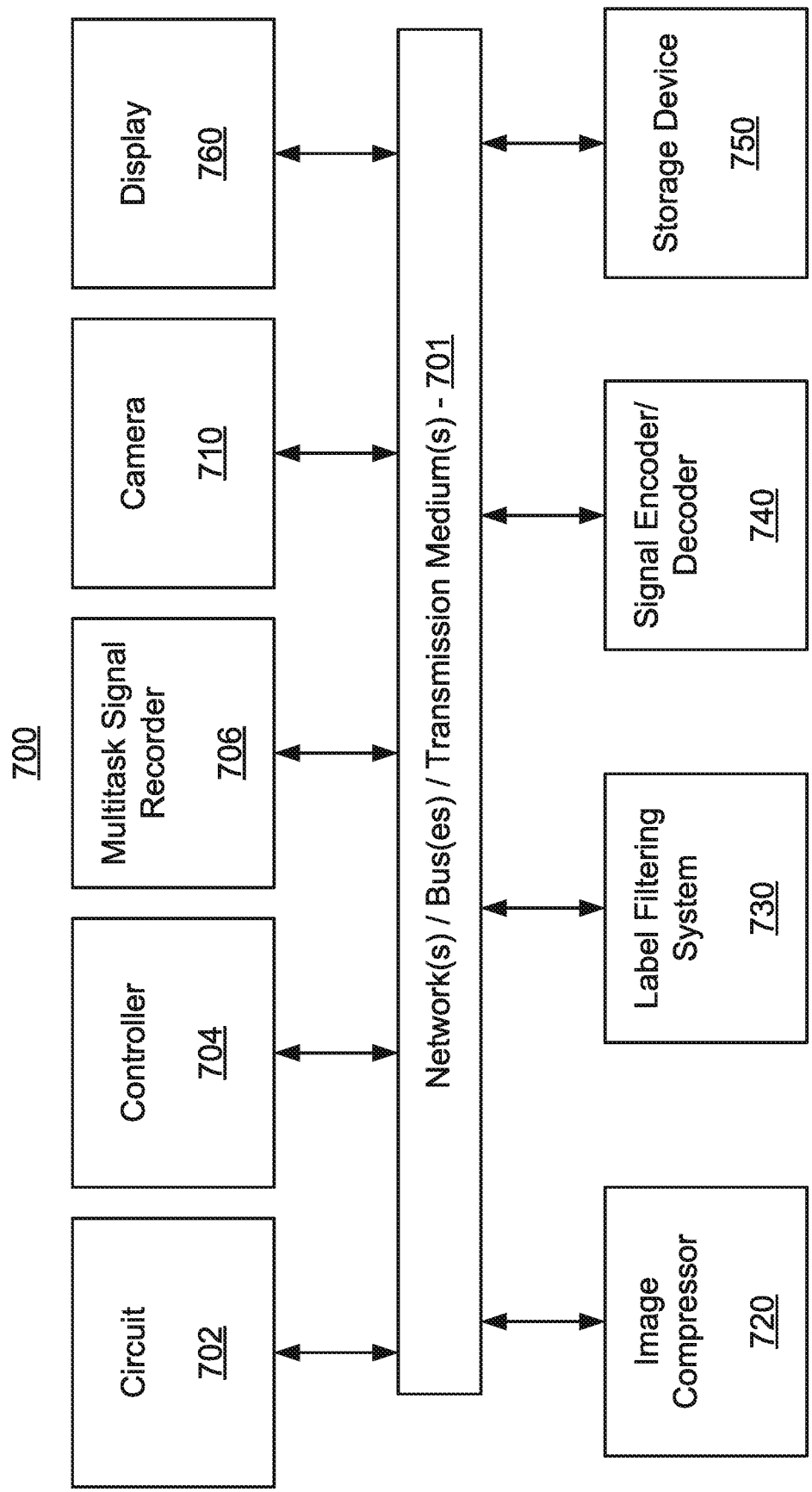
FIG. 7 is a block/flow diagram illustrating an exemplary system for acquiring data from an input signal using multitask regression, in accordance with an embodiment of the present principles.

Further, it is to be appreciated that processing system 600 may perform at least part of the methods described herein including, for example, at least part of method 100 of FIG. 1, method 140 of FIG. 2, method 150 of FIG. 3, process 400 of FIG. 4, and method 500 of FIG. 5. Similarly, part or all of system 700 of FIG. 7 may be used to perform at least part of the methods described herein including, for example, at least part of method of method 100 of FIG. 1, method 140 of FIG. 2, method 150 of FIG. 3, process 400 of FIG. 4, and method 500 of FIG. 5. Referring now to FIG. 7, an exemplary system 700 for acquiring data from an input signal using multitask regression is illustratively depicted in accordance with an embodiment of the present principles.

While many aspects of system 700 are described in singular form for the sake of illustration and clarity, the same can be applied to multiple ones of the items mentioned with respect to the description of system 700. For example, while a single signal encoder/decoder 740 may be mentioned with respect to system 700, more than one signal encoder/decoder 740 can be used in accordance with the teachings of the present principles, while maintaining the spirit of the present principles. Furthermore, the signal encoder/decoder 740 may incorporate one or more signal encoders and/or signal decoders. Moreover, it is appreciated that the signal encoder/decoder 740 is but one aspect involved with system 700 than can be extended to plural form while maintaining the spirit of the present principles.

In an embodiment, the system 700 may include a plurality of components, which may include one or more circuits 702, controllers 704, multitask signal recorders 706, cameras 710, image compressors 720, signal encoders/decoders 740, storage devices 750 (e.g., computer readable storage medium), and/or displays 760. The above components may be connected by, for example, one or more networks, buses, or transmission mediums 701, wherein the one or more networks may include one or more wired or wireless networks such as, e.g., WiFi, Bluetooth, etc, and the one or more transmission mediums may include bounded transmission media, such as, e.g., coaxial cable, fiber optics, etc., and unbounded transmission media, such as, e.g., radio transmission, microwave transmission, etc. Furthermore, data (e.g., system condition data, temperature, voltage, etc.) may be collected according to various embodiments of the present principles. The bus may be connected to any components via a wired or wireless connection. In an embodiment, a camera 710 may be employed to capture a digital image that can be compressed into a digital signal using the image compressor 720 and the signal encoder/decoder 740. The camera 710 may be connected to a bus 701 via a wired or wireless connection. At least one storage device 750 may be employed to store, e.g., multitask signals, constructed images, etc.

In an embodiment, a multitask signal recorder 706 may be employed to record a multitask signal. The multitask signal recorder 706 may include, a camera 710, a medical imaging device (e.g., an fMRI device, a Magnetic Resonance Imaging (MRI) device, an X-Ray machine, a Computed Tomography (CT) device, a Positron Emission Tomography (PET) scanner, etc.), etc.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A method for acquiring data from an input signal using multitask regression, comprising:

receiving, into a memory, the input signal, the input signal including data that includes a plurality of features;

determining at least two computational tasks to analyze within the input signal;

regularizing all of the at least two tasks using shared adaptive weights;

performing, using a processor, a multitask regression on the input signal to create a solution path for all of the at least two tasks, wherein the multitask regression includes:

concurrently updating a model coefficient and a regularization weight together under an equality norm constraint until convergence is reached to produce a sparse model in the solution path;

concurrently updating the model coefficient and regularization weight together under an updated equality norm constraint that has a greater $l_1$-penalty than the previous equality norm constraint until convergence is reached to produce another sparse model in the solution path; and gradually strengthening a global magnitude of the $l_1$-penalty by adjusting the equality norm constraint on the regularization weight by annealing to improve the convergence and reduce a sensitivity on initial conditions, wherein the shared adaptive weights w=[$w_1$, $w_2$, ..., $w_D$]$^T$ are used for the regularizing over all K tasks, as $$\min_{w,B} \sum_{k=1}^{K} \left( \|X^k \beta^k - y^k\|_2^2 + |w^{-\gamma} \odot \beta^k| \right),$$

s.t. $\Sigma_d w_d = \omega$, $w_d \geq 0$, wherein $\beta^k \in \mathbb{R}^{D \times 1}$ represents the model coefficient for a $l^{th}$ task for k=1, 2, ... K, and B=[$\beta^1$, $\beta^2$, ..., $\beta^k$];

selecting a sparse model from the solution path;

constructing an image using the sparse model; and displaying the image on a display.

2. The method as recited in claim 1, wherein the updating the model coefficient and the regularization weight further comprises:

updating the model coefficient by training a Least Absolute Shrinkage and Selection Operator problem with a fixed regularization weight and solving the Least Absolute Shrinkage and Selection Operator problem for the model coefficient; and updating the regularization weight by training a constrained optimization problem with a fixed model coefficient and solving the constrained optimization problem for the regularization weight.

3. The method as recited in claim 1, further comprising recording the input signal, using a signal recorder, prior to receiving the input signal.

4. The method as recited in claim 1, wherein the performing the multitask regression increases a global regularization strength across the at least two tasks.

5. The method as recited in claim 1, wherein updating the equality norm constraint decreases a number of input signal features in the produced model.

6. The method as recited in claim 5, wherein the updating the model coefficient and regularization weight together under an updated equality norm constraint is repeated until a model is produced that is without features in the input signal.

7. The method as recited in claim 1, wherein the selecting a sparse model from the solution path further includes performing a cross-validation of all of the sparse models in the solution path.

8. A system for acquiring data from an input signal using multitask regression, comprising:
    a memory to receive the input signal, the input signal including data that includes a plurality of features;
    a processor configured to:
        determine at least two computational tasks to analyze within the input signal;
        regularize all of the at least two tasks using shared adaptive weights;
        perform a multitask regression on the input signal to create a solution path for all of the at least two tasks, wherein the processor performs the multitask regression by:
            concurrently updating a model coefficient and a regularization weight together under an equality norm constraint until convergence is reached to produce a sparse model in the solution path;
            concurrently updating the model coefficient and regularization weight together under an updated equality norm constraint that has a greater $l_1$-penalty than the previous equality norm constraint until convergence is reached to produce another sparse model in the solution path; and
        gradually strengthening a global magnitude of the $l_1$-penalty by adjusting the equality norm constraint on the regularization weight by annealing to improve the convergence and reduce a sensitivity on initial conditions,
        wherein the shared adaptive weights $w=[w_1, w_2, \ldots, w_D]^T$ are used for the regularizing over all K tasks, as $$\min_{w,B} \sum_{k=1}^{K} (\|X^k \beta^k - y^k\|_2^2 + |w^{-\gamma} \odot \beta^k|),$$

s.t. $\Sigma_d w_d = \omega$, $w_d \geq 0$, wherein $\beta^k \in \mathbb{R}^{D \times 1}$ represents the model coefficient for a $k^{th}$ task for $k=1, 2, \ldots, K$, and $B=[\beta^1, \beta^2, \ldots, \beta^k]$;
        select a sparse model from the solution path; and
        construct an image using the sparse model; and
    a display for displaying the constructed image.

9. The system as recited in claim 8, wherein the processor updates the model coefficient and the regularization weight together by:
    updating the model coefficient by training a Least Absolute Shrinkage and Selection Operator problem with a fixed regularization weight and solving the Least Absolute Shrinkage and Selection Operator problem for the model coefficient; and
    updating the regularization weight by training a constrained optimization problem with a fixed model coefficient and solving the constrained optimization problem for the regularization weight.

10. The system as recited in claim 8, further comprising a signal recorder for recording the input signal.

11. The system as recited in claim 10, wherein the processor, by performing the multitask regression, increases a global regularization strength across the at least two tasks.

12. The system as recited in claim 8, wherein updating the equality norm constraint decreases a number of input signal features in the produced model.

13. The system as recited in claim 12, wherein the processor is further configured to repeat the process of updating the model coefficient and regularization weight together under an updated equality norm constraint until a model is produced that is without features in the input signal.

14. The system as recited in claim 8, wherein the processor is further configured to perform a cross-validation of all of the sparse models in the solution path prior to selecting a sparse model from the solution path.

15. A non-transitory computer-readable storage medium including a computer-readable program for assigning labels to an object, wherein the computer-readable program when executed on a computer causes the computer to perform the steps of:
    receiving, into a memory, the input signal, the input signal including data that includes a plurality of features;
    determining at least two computational tasks to analyze within the input signal;
    regularizing all of the at least two tasks using shared adaptive weights;
    performing, using a processor, a multitask regression on the input signal to create a solution path for all of the at least two tasks, wherein the multitask regression includes:
        updating a model coefficient and a regularization weight together under an equality norm constraint until convergence is reached to produce a sparse model in the solution path;
        updating the model coefficient and regularization weight together under an updated equality norm constraint that has a greater $l_1$-penalty than the previous equality norm constraint until convergence is reached to produce another sparse model in the solution path; and
    gradually strengthening a global magnitude of the $l_1$-penalty by adjusting the equality norm constraint on the regularization weight by annealing to improve the convergence and reduce a sensitivity on initial conditions,
        wherein the shared adaptive weights $w=[w_1, w_2, \ldots, w_D]^T$ are used for the regularizing over all K tasks, as $$\min_{w,B} \sum_{k=1}^{K} (\|X^k \beta^k - y^k\|_2^2 + |w^{-\gamma} \odot \beta^k|),$$

s.t. $\Sigma_d w_d = \omega$, $w_d \geq 0$, wherein $\beta^k \in \mathbb{R}^{D \times 1}$ represents the model coefficient for a $k^{th}$ task for k=1, 2, ..., K, and B=[$\beta^1, \beta^2, \ldots, \beta^k$];

selecting a sparse model from the solution path;
constructing an image using the sparse model; and
displaying the image on a display.

16. The computer-readable storage medium as recited in claim 15, wherein the updating the model coefficient and the regularization weight further comprises:
  updating the model coefficient by training a Least Absolute Shrinkage and Selection Operator problem with a fixed regularization weight and solving the Least Absolute Shrinkage and Selection Operator problem for the model coefficient; and
  updating the regularization weight by training a constrained optimization problem with a fixed model coefficient and solving the constrained optimization problem for the regularization weight.

17. The computer-readable storage medium as recited in claim 15, further comprising recording the input signal, using a signal recorder, prior to receiving the input signal.

18. The computer-readable storage medium as recited in claim 17, wherein the performing the multitask regression increases a global regularization strength across the at least two tasks.

19. The computer-readable storage medium as recited in claim 15, wherein updating the equality norm constraint decreases a number of input signal features in the produced model.

20. The computer-readable storage medium as recited in claim 19, wherein the updating the model coefficient and regularization weight together under an updated equality norm constraint is repeated until a model is produced that is without features in the input signal.

* * * * *